United States Patent [19]
Jensma

[11] Patent Number: 5,738,682
[45] Date of Patent: Apr. 14, 1998

[54] APPARATUS FOR COOLING SURFACES

[75] Inventor: Klaas Jensma, Wolvega, Netherlands

[73] Assignee: Koninklijke Utermohlen N.V., Netherlands

[21] Appl. No.: 736,277

[22] Filed: Oct. 24, 1996

Related U.S. Application Data

[63] Continuation of Ser. No. 103,903, Aug. 10, 1993, abandoned.

[30] Foreign Application Priority Data

Jan. 29, 1993 [NL] Netherlands ............... 9300190

[51] Int. Cl.⁶ .................................................. A61B 17/36
[52] U.S. Cl. .................. 606/23; 606/20; 606/25; 62/293
[58] Field of Search ............... 606/20–26; 62/293, 62/50.1, 50.7, 52.1

[56] References Cited

U.S. PATENT DOCUMENTS

| | | |
|---|---|---|
| 3,736,936 | 6/1973 | Basiulis et al. |
| 4,082,096 | 4/1978 | Benson. |
| 4,116,199 | 9/1978 | Bryne. |
| 4,865,028 | 9/1989 | Swart. |

FOREIGN PATENT DOCUMENTS

| | | | |
|---|---|---|---|
| 0 281 212 | 7/1988 | European Pat. Off. | |
| 0281212 | 9/1988 | European Pat. Off. | |
| 2165485 | 3/1973 | France. | |
| 7300240 | 7/1973 | Netherlands. | |
| 88203694 | 12/1987 | U.S.S.R. | 606/23 |
| 91338144 | 12/1990 | U.S.S.R. | 606/25 |
| 1 415 914 | 12/1975 | United Kingdom. | |
| 2040169 | 8/1980 | United Kingdom. | |
| 2244922 | 12/1991 | United Kingdom. | |

OTHER PUBLICATIONS

Trade Brochure published by Applimed SA in 1992.
European Search Report issued on European Application No. 94200181.9.

Primary Examiner—Michael Peffley
Attorney, Agent, or Firm—Timothy H. P. Richardson

[57] ABSTRACT

In methods and apparatus for cooling surfaces, a pressurized liquid refrigerant is dispensed through a shaped member composed of an open celled foam. The method is particularly useful for localized freezing of a wart or other growth prior to its removal from skin of a human being or another animal.

23 Claims, 2 Drawing Sheets

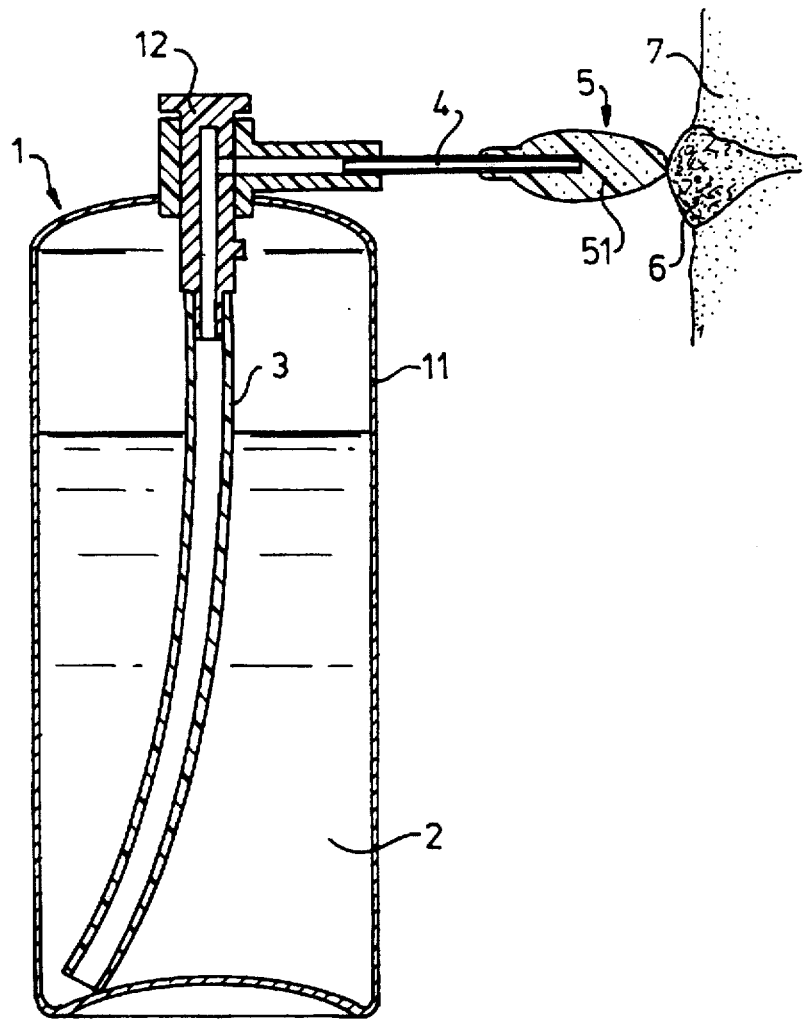
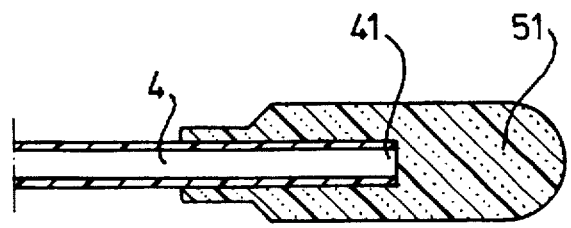

APPARATUS FOR COOLING SURFACES

This application is a continuation under 37 CFR 1.62 of application Ser. No. 08/103,903 filed Aug. 10, 1993 (abandoned).

BACKGROUND OF THE INVENTION

1. Field of the Invention

This invention relates to methods and apparatus for cooling surfaces by evaporating a liquid refrigerant.

2. Introduction to the Invention

It is well known to produce a cooling effect by the evaporation of a liquid. A recent and particularly valuable therapeutic use of this effect is to provide localized freezing of a part of a human or animal body, e.g. in order to remove a wart or other growth. In this use, a refrigerant is maintained under pressure in a can and is dispensed, via a valve and an outlet tube, through a cotton wool bud which surrounds the discharge end of the outlet tube and which is placed on or near the site to be treated. Details of that method and of apparatus for use in that method are disclosed in U.S. Pat. No. 4,865,028 (Swart), the disclosure of which is incorporated herein by reference for all purposes.

SUMMARY OF THE INVENTION

In use of the invention described in U.S. Pat. No. 4,865,028, it has been found that the rate of evaporation (and, therefore, the rate of cooling) can be dependent on the pressure between the cotton bud and the skin; in particular, if the pressure is too great, the rate of cooling is adversely affected. It has also been found that it is difficult to obtain good results when precise placement of the cotton bud is needed, e.g. for small warts; and when the treatment site is difficult to reach; and when the treatment site is large.

I have discovered that improved results can be obtained, and in particular that the foregoing problems can be mitigated, by dispensing the liquid refrigerant through a shaped member which is composed of an open celled foam. Especially good results are obtained when the shaped member is hollow, thus providing an expansion chamber and reservoir for the refrigerant; the reservoir preferably contains a permeable and absorbent material, e.g. cotton wool.

In one preferred aspect the present invention provides an assembly for dispensing a refrigerant, said assembly comprising (1) a container which (a) includes a valve having an inlet and an outlet, and (b) is sealed except for the valve;

(2) a liquid refrigerant which (a) is contained under pressure within the container and (b) has a boiling point at atmospheric pressure of less than 0° C.;

(3) a feed tube which has (a) a first end within the refrigerant, and (b) a second end which communicates with the inlet of the valve;

(4) an outlet tube which has (a) a first end which communicates with the outlet of the valve, and (b) a discharge end;

and (5) a dispensing head which (a) comprises a shaped member composed of an open celled foam, and (b) is secured to the discharge end of the outlet tube so that, when the valve is open, the refrigerant is dispensed through the open celled foam.

In another preferred aspect, the present invention provides a method of cooling the skin of a living mammal, said method comprising (1) placing adjacent to the skin the dispensing head of an assembly as defined above, and (2) opening the valve of said assembly so that refrigerant passes through the feed tube, the outlet tube and the open celled foam of the dispensing head and evaporates adjacent to the skin.

BRIEF DESCRIPTION OF THE DRAWING

This invention is illustrated in the accompanying drawings, in which

FIG. 1 is a diagrammatic cross-section through an assembly of the invention being used to freeze a wart; and FIGS. 2 to 6 are diagrammatic partial cross-sections through applicators of the invention.

DETAILED DESCRIPTION OF THE INVENTION

Figure 3:
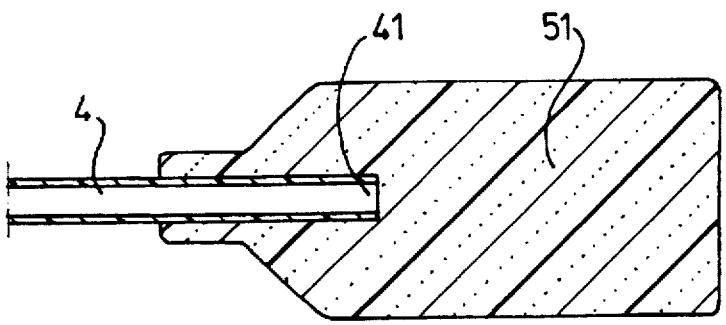

Open celled foam materials are well known and those skilled in the art will have no difficulty, after consideration of the disclosure in this specification, in selecting open celled foams which are suitable for use in this invention.

The open celled foam is preferably composed of a foamed synthetic organic polymer which does not react chemically with the refrigerant and which has suitable physical properties throughout the range of temperatures to which it is exposed in the method, e.g. −20° C. to 25° C. The foam is preferably flexible at 15°–25° C., so that the dispensing head can be easily fitted over the outlet tube before being secured thereto. An elongation of 200 to 500%, particularly 300–400%, at 20° C. (as measured by ISO 1798) is preferred. As the temperature is reduced, the flexibility of the foam will decrease, and this is desirable because compression of the foam in use will reduce the cooling effect. However, in some cases, it is desirable for the foam to remain relatively flexible while the refrigerant is being dispensed, e.g. at −20° to 0° C., so that the foam can be pushed against the surface to be cooled and will conform to that surface without inelastic crushing of the open cell structure; this is in general desirable when a relatively large surface is to be cooled. In other cases, it is desirable for the foam to be relatively stiff when cooled by evaporation of the refrigerant; this is in general desirable when the dispensing cap must be precisely positioned. The less the deformation of the foam while the refrigerant is being dispensed, the less the variation in the rate at which the refrigerant is dispensed (and, therefore, in the rate of cooling).

The density of the foam is preferably less than 60, particularly 10–40, especially 12–35 kg/m$^3$, and I have obtained particularly good results with a foam of density about 26–32 kg/m$^3$. The size of the pores is preferably 5 to 50, particularly 20–40, e.g. 30–40, especially 27–32, pores/cm, as measured by 1S0 45.2444. Especially when there is a space between the foam member and the discharge tube and that space contains a permeable and absorbent material, the foams which can be used include the so-called reticulated foams. Reticulated foams are available from Recticel S.A., Belgium. Often they have a high porosity, e.g. greater than 90%. It is believed that they are made by a process which involves an explosive reaction in a closed vessel in the presence of oxygen and hydrogen.

Suitable polymers for use as foams in the present invention include polyesters, polyethers, and polyurethanes, particularly polyester-based polyurethanes. Preferably the foam is composed of a polymer which is wetted by the liquid refrigerant, since this appears to result in a lower temperature and/or a longer effective treatment time.

Another important factor in selecting the foam is the need to secure it to the outlet tube. Preferably the foam is secured to the outlet tube by ultrasonic welding or another method of heat-sealing. Foams having a pore size of 20–40 pores/cm can generally be ultrasonically welded. Alternatively the foam can be glued to the outlet tube, and this often yields better results when the pore size is less, e.g. 2–5 pores/cm.

I have obtained particularly good results using a foam supplied by Applimed SA of Chatel St. Denis, Switzerland, under the trade name Filterfoam PPI80. The Technical Information Sheet provided by the supplier gives the following information for Filterfoam PPI80.

| Polymer | Polyester-based polyurethane |
|---|---|
| Structure | All open cells, 65–85 pores/inch (25.6–33.5 cm/inch) (ISO 45.2441) |
| Weight | 26–32 kg/m$^3$ (ISO 1855/71) |
| Elongation | Minimum 200% (ISO R1798/71), typically 300–400% |
| Rest of Pressure Deformation | About 6% |
| Compression resistance | 2–4 kPa |
| Tensile strength | At least 200 kPa |
| Temperature limits | −20° C. to +100° C. |
| Free of precipitation | yes |
| Resistant to mineral oil | yes |
| Color | Cream |

The open celled foam can be in any shape which is appropriate to the way it is to be used. Thus a user of this invention can have available to him or her a variety of dispensers having different dispensing heads and can select a dispenser appropriate to any particular situation. The exterior surface of the open celled foam member is preferably also the exterior surface of the dispensing head. However, part or all of the foam member can be covered by a different material.

Preferably, the exterior surface of the shaped foam is rotationally symmetrical about an axis which is also the axis of the outlet tube, and has a length which is 1.5 to 5 times, particularly 2.0 to 4 times, its maximum diameter. For example, the exterior surface can comprise a base portion whose shape corresponds to, but is slightly larger than, the outlet tube; a center portion whose shape is generally similar to the shape of the outlet tube but at least a part of which is substantially larger in diameter than the base portion; and a tip portion which provides a smoothly curved or substantially flat transverse surface, substantially at right angles to the axis of the outlet tube. The diameter of the tip is generally 1.5 to 15 mm, preferably 1.75 to 12 mm. Generally, the larger the diameter of the tip, the deeper the cooling effect on the surface. In one embodiment, the center portion increases in diameter above the base potion (e.g. at an angle of 15°–45° to the axis) to a maximum value which is 2.5 to 7.5 times, preferably 3 to 5 times, the external diameter of the outlet tube, and then maintains a regular cylindrical shape, and the tip portion provides a substantially flat or smoothly curved transverse surface, e.g. a surface which is a part of a sphere. In this embodiment, the diameter of the tip is for example 4 to 8 mm. In a similar embodiment, the regular cylindrical part of the center portion is not present, the center portion increasing in diameter slowly until the tip portion is reached. In this embodiment, the diameter of the tip is for example 7 to 12 mm. In another embodiment, the center portion increases in diameter above the base portion (e.g. at an angle of 15°–45° to the axis) to a maximum value which is 2.5 to 7.5 times, preferably 3 to 5 times, the external diameter of the outlet tube, and then tapers inwards again (e.g. at an angle of 15°–45° to the axis) to a minimum diameter which is 0.5 to 1.5 times the external diameter of the outlet tube; and the tip portion provides a substantially flat or smoothly curved transverse surface. In this embodiment, the diameter of the tip is for example 1.5 to 4 mm. The overall axial length of the foam member is generally 10 to 35 mm, preferably 15 to 30 mm, e.g. 17 to 25 mm.

Preferably the shaped foam is hollow so that it fits over the discharge end of the outlet tube so that there is a space between the foam and the discharge end. The internal surface of such a shaped foam member defines an internal cavity having a proximal end portion and a distal end portion. The proximal end portion of the cavity fits snugly over the outer tube near the discharge end thereof, and is secured to the outlet tube. The distal portion of the cavity extends beyond the discharge end of the outlet tube. Preferably the cavity also has a center portion which surrounds the end portion of the outlet tube and is spaced apart from the outer tube. The cavity is generally rotationally symmetrical about an axis which is also the axis of the outlet tube. The axial length of the proximal portion is preferably at least 0.75 times, particularly at least 1.2 times, e.g. 1.5 to 3 times, the external diameter of the outer tube, so as to ensure a secure connection between the supply tube and the dispensing head. This length will generally be 2 to 12 mm, preferably 3 to 8 mm, particularly 4 to 7 mm. The axial length of the center portion of the cavity (when present) is preferably 2 to 10 times, particularly 3 to 6 times, especially 3 to 4 times, the external diameter of the outlet tube. This length will generally be 3 to 18 mm, preferably 6 to 15 mm, particularly 8 to 13 mm. The axial length of the distal potion of the cavity is preferably at least 0.4 times, particularly 0.5 to 2 times, the external diameter of the outlet tube. This length will generally be 1.5 to 8 mm, preferably 2 to 6 mm, particularly 2.5 to 5 mm. The total axial length of the central portion and the distal portion is preferably 2 to 10 times, particularly 3 to 7 times, the external diameter of the outlet tube.

The volume of the internal cavity of the dispensing head which is not occupied by the outlet tube, expressed in mm$^3$, is preferably 15 to 40 times, particularly 20 to 30 times, the cross-sectional area of the outlet tube, expressed in mm$^2$ and calculated on the external diameter of the outlet tube, i.e. the volume is preferably $15\pi D^2/4$ to $40\pi D^2/4$, particularly $20\pi D^2/4$ to $30\pi D^2/4$, mm$^3$, where D is the external diameter of the outlet tube in mm. This volume will generally be 60 to 200 mm$^3$, preferably 80 to 150 mm$^3$.

When the invention is being used, the foam member is subject to internal pressure from the refrigerant and may be subject to external pressure when pressed against the surface which is being cooled. The wall thickness of the foam member should be selected accordingly. Generally, the wall thickness of the foam member, in the portions through which the refrigerant is dispensed, is at least 0.5 mm, preferably at least 0.75 mm, but less than 5 mm, preferably less than 4 mm, e.g. 3–4 mm. The wall thickness can vary from place to place, and is generally greatest opposite the orifice of the outlet tube, e.g. at least 1.5 mm.

I have found that when (as is preferred) there is a space between the outlet tube and the dispensing head, a yet further improvement in results can be obtained by filling at least part of that space with a suitable permeable and absorbent solid material. The material modifies and controls the pressure and flow of the refrigerant to the interior surface of the foam member so that the cooling effect is more uniform and more reproducible. I have obtained excellent results using cotton wool as the permeable and absorbent material, for example cotton wool in the form of a bud secured to the top of a hollow tube; in some cases, excellent results can be obtained using the absorbent cotton wool-tipped tubes which are commercially available. However, other materials, including other non-woven fibrous cellulosic or non-cellulosic materials could also be used. The use of the term "absorbent" is not intended to imply that there is any chemical interaction between the material and the refrigerant.

The presence of the cotton wool or other permeable material can also improve the physical strength of the dispenser. The shaped foam member can be sealed around the cotton wool, which thus provides a better connection between the foam member and the outlet tube.

The outlet tube to which the dispensing head is secured can be made of any suitable material, e.g. polypropylene, and can be of any suitable dimensions, e.g. an external diameter of 2 to 4 mm, preferably 2.25 to 2.75 mm, a wall thickness of 0.15 to 0.4 mm, preferably 0.2 to 0.3 mm. For most uses, a length of 30 to 150 mm, preferably 50 to 90 mm, is satisfactory. For gynaecological use, a length of 100 mm or more, e.g. 100–200 mm, particularly 130–170 mm, is usually preferred. The outlet tube should be sufficiently rigid to allow accurate placement of the dispenser head.

The refrigerants used in this invention preferably have a boiling point at atmospheric pressure of 0° C. to −75° C. or even lower. Suitable refrigerants are well known to those skilled in the art and include the refrigerants disclosed in U.S. Pat. No. 4,865,028 incorporated by reference herein, including halogenated hydrocarbons (for example tetrafluoromethane, trifluoromethane, monochlorotrifluoromethane, hexafluoroethane, monobromotrifluoromethane, monochlorodifluoromethane, monochloropentafluorothane, dichlorodifluoromethane, 1,2-dichloro-1,1,2,2-tetrafluoroethane, trichloromonofluoromethane, 1,1,2-trichloro-1,2,2-trifluoromethane and 1,1-difluoroethane), propane, n-butane, isobutane, dimethyl ether and nitrogen. Dimethyl ether and said alkanes, in particular propane, are preferred for environmental reasons.

Containers and valves for dispensing pressurized liquids are well known, and those skilled in the art will have no difficulty, after consideration of the disclosure in this specification, in selecting containers and valves suitable for use in this invention. The refrigerant is maintained under pressure in the container until it is dispensed. The pressure in the container is above atmospheric, but preferably not more than 12 bar, at 50° C. (about 5 bar at ambient temperature). The valve which controls the release of the refrigerant from the pressurized container is preferably one which can be operated by the user's finger. The valve preferably has a relatively low flow capacity of no more than 60 ml/min, particularly no more than 30 ml/min.

The assemblies of the invention can be used for cooling any surface, but are particularly useful cooling the skin of a human being or other living mammal, especially for freezing warts and the like (including for example *Verruca plana*, *Molluscum contagiosum*, condylomata, *Varruca vulgaria*, *Varruca filliformia* and *Varruca plantaris*), so that they can be removed. An improved cooling effect can often be obtained by pressing the dispensing head intermittently against the surface, using a pressure which elastically deforms the foam, and at intervals which allow at least partial recovery of the foam between pressings.

Referring now to the drawings, FIG. 1 is a diagrammatic cross-section of an assembly according to the invention. In FIG. 1, container 1 comprises a sealed body portion 11 and a finger-operated valve 12. Liquid refrigerant 2 is contained under pressure of its own vapor in the container 1. Feed tube 3 has a first end immersed in the refrigerant 2 and a second end communicating with the inlet of the valve 12. Outlet tube 4 has a first end communicating with the outlet of the valve 12 and a discharge end secured to a dispensing head 5 which comprises a shaped member 51 composed of an open celled foam. When the valve is open, as it is in FIG. 1, liquid refrigerant 2 is forced through the feed tube 3, valve 12, outlet tube 4, and dispensing head 5, and evaporates within or adjacent to the foam member 51, thus cooling the head 5, the atmosphere around the head 5 and anything contacted by the head 5. As shown in FIG. 1, the head 5 is pressed lightly against a wart 6 in the skin 7 of a human body. The wart is thus frozen so that it can be removed.

Figure 4:
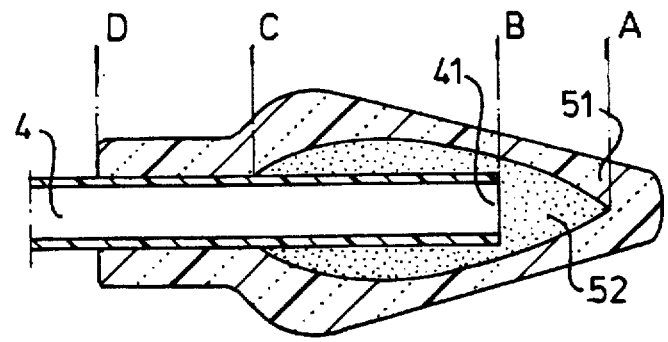
Figure 5:
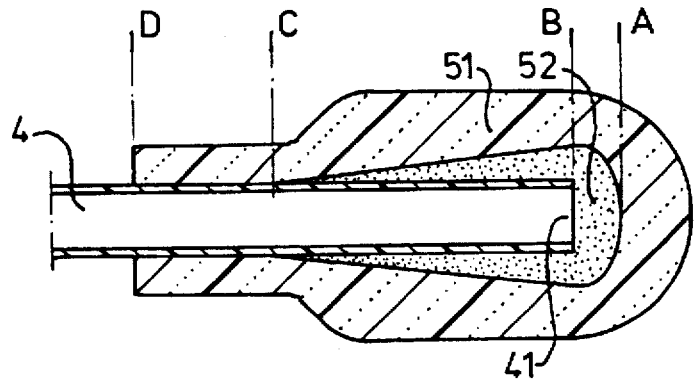
Figure 6:
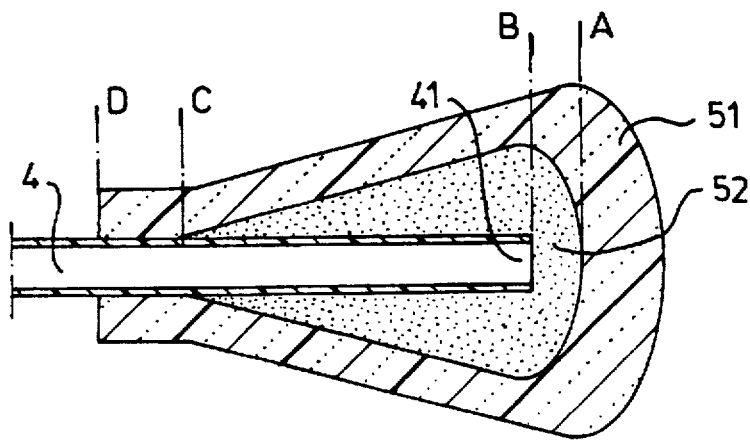

FIGS. 2–6 are diagrammatic partial cross-sections of applicators of the invention which comprise an outlet tube 4 having a discharge end 41 which is surrounded by a shaped member 51 composed of an open celled foam. In FIGS. 4, 5 and 6, there is a space surrounding the discharge end 41 and this space is filled with cotton wool 41. In FIGS. 4, 5 and 6, the interior surface of the foamed member defines a proximal portion which lies between dotted lines C and D, a center portion which lies between dotted lines B and C, and a distal portion which lies between dotted lines A and B. In one specific example of an applicator as shown in FIG. 4, the cotton wool had a maximum diameter of 5.25 to 5.75 mm, a length of about 14 mm, and a weight of about 0.0045 g; and the open celled foam member was composed of the Filterfoam PPI80 material referred to above and also had a weight of about 0.0045 g. The cotton wool bud was coated with 1% solution of Methocel (available from Dow Chemical) to help maintain its shape, before the foam member was placed over the cotton wool bud and the outlet tube and heat sealed in place.

What is claimed is:

1. An assembly for dispensing a refrigerant, said assembly comprising
   (1) a container which
      (a) includes a valve having an inlet and an outlet, and
      (b) is sealed except for the valve;
   (2) a liquid refrigerant which
      (a) is contained under pressure within the container and
      (b) has a boiling point at atmospheric pressure of less than 0° C.;
   (3) a feed tube which has
      (a) a first end within the refrigerant, and
      (b) a second end which communicates with the inlet of the valve;
   (4) an outlet tube which has
      (a) a first end which communicates with the outlet of the valve, and
      (b) a discharge end;
   and
   (5) a dispensing head which
      (a) comprises a shaped member composed of an open celled foam, and
      (b) is secured to the discharge end of the outlet tube so that, when the valve is open, the refrigerant is dispensed through the open celled foam.

2. An assembly according to claim 1 wherein the foam has a density of 10–40 kg/m³ and a pore size of 20–40 pores/cm.

3. An assembly according to claim 1 wherein the foam is composed of a polyester-based polyurethane.

4. An assembly according to claim 1 wherein the foam has an elongation of 200 to 500% at 20° C.

5. An assembly according to claim 1 wherein the foam has an elongation of 300 to 400% at 20° C.

6. An assembly according to claim 1 wherein the foam is wetted by the refrigerant.

7. An assembly according to claim 1 wherein the shaped foam member is hollow and fits over the discharge end of the outlet tube so that there is a space between the discharge end and the foam.

8. An assembly according to claim 7 wherein at least a part of the space between the discharge end and the foam is filled by a permeable solid material.

9. An assembly according to claim 8 wherein the permeable solid material is cotton wool.

10. An assembly according to claim 7 wherein the space between the outlet tube and the interior surface of the shaped foam member has a volume which is from $15\pi D^2/4$ to $40\pi D^2/4$ mm³, where D is the external diameter of the outlet tube in mm.

11. An assembly according to claim 7 wherein the wall thickness of the shaped foam member is 3 to 4 mm.

12. As assembly according to claim 7 wherein the internal surface of the shaped foam member defines a cavity having a proximal end portion which is secured to the outlet tube, a center portion which surrounds the end portion of the outlet tube and is spaced apart from the outlet tube, and a distal portion which extends beyond the discharge end of the outlet tube.

13. An assembly according to claim 12 wherein the axial length of the proximal portion is at least 0.75D, the axial length of the center portion is 2D to 10D, and the axial length of the distal portion is at least 0.4D, where D is the external diameter of the outlet tube.

14. An assembly according to claim 13 wherein the length of the proximal portion is 1.5D to 3D, the length of the center portion is 3D to 6D, and the length of the distal portion is 0.5D to 2D.

15. An assembly according to claim 13 wherein the outlet tube has an external diameter of 2 to 4 mm and a wall thickness of 0.15 to 0.4 mm.

16. An assembly according to claim 12 wherein the axial length of the proximal portion is 2 to 12 mm, the axial length of the center portion is 3 to 18 mm, and the axial length of the distal portion is 1.5 to 8 mm.

17. An assembly according to claim 16 wherein the length of the proximal portion is 3 to 8 mm, the length of the center portion is 6 to 15 mm, and the length of the distal portion is 2 to 6 mm.

18. An assembly according to claim 16 wherein the space between the outlet tube and the interior surface of the shaped foam member has a volume of 60 to 200 mm³.

19. A method of cooling the skin of a living mammal, said method comprising (1) placing adjacent to the skin the dispensing head of an assembly as claimed in claim 1, and (2) opening the valve of said assembly so that refrigerant in the container of said assembly passes through the feed tube, the outlet tube and the open celled foam of the dispensing head of said assembly and evaporates adjacent to the skin.

20. A method according to claim 19 wherein the living mammal is a human being.

21. A method according to claim 20 wherein the skin which is cooled comprises a wart.

22. An assembly for dispensing a refrigerant, said assembly comprising (1) a container which
   (a) includes a valve having an inlet and an outlet, and
   (b) is sealed except for the valve;

(2) a liquid refrigerant which
   (a) is contained under pressure within the container and
   (b) has a boiling point at atmospheric pressure of less than 0° C.;

(3) a feed tube which has
   (a) a first end within the refrigerant, and
   (b) a second end which communicates with the inlet of the valve;

(4) an outlet tube which has
   (a) a first end which communicates with the outlet of the valve, and
   (b) a discharge end;

and (5) a dispensing head which
   (a) comprises a shaped member composed of an open celled foam which
      (i) has a density of 10–40 kg/m³,
      (ii) has a pore size of 20–40 pores/cm, and
      (iii) is composed of a polyester-based polyurethane and (b) is secured to the discharge end of the outlet tube so that, when the valve is open, the refrigerant is dispensed through the open celled foam.

23. A method of cooling the skin of a human being, said method comprising (1) placing adjacent to the skin the dispensing head of an assembly as claimed in claim 22, and (2) opening the valve of said assembly so that the refrigerant in the container of said assembly passes through the outlet tube and the open celled foam of the dispensing head of said assembly and evaporates adjacent to the skin.

* * * * *

UNITED STATES PATENT AND TRADEMARK OFFICE
CERTIFICATE OF CORRECTION

PATENT NO. : 5,738,682
DATED : April 14, 1998
INVENTOR(S) : Klaas Jensma

It is certified that error appears in the above-identified patent and that said Letters Patent is hereby corrected as shown below:

Title page,
Item [75], line 3, should read -- Klaas Jensma, De Wilgen, The Netherlands; Matth J.A. Bronsgeest, Nieuwerburg, The Netherlands; William H. Hinchey, Easton, Pennsylvania --.

Signed and Sealed this

Twenty-seventh Day of November, 2001

Attest:

*Attesting Officer*

NICHOLAS P. GODICI
*Acting Director of the United States Patent and Trademark Office*